: United States Patent (10) Patent No.: US 7,883,514 B2
Worst et al. (45) Date of Patent: *Feb. 8, 2011

(54) FIXATION OF AN INTRAOCULAR IMPLANT TO THE IRIS

(75) Inventors: Jan Gerben Frans Worst, Haren (NL); Harry Franciscus Simon, Groningen (NL)

(73) Assignee: Ophtec B.V. (NL)

( * ) Notice: Subject to any disclaimer, the term of this patent is extended or adjusted under 35 U.S.C. 154(b) by 0 days.

This patent is subject to a terminal disclaimer.

(21) Appl. No.: 10/872,305

(22) Filed: Jun. 18, 2004

(65) Prior Publication Data

US 2004/0225357 A1 Nov. 11, 2004

Related U.S. Application Data

(62) Division of application No. 10/055,416, filed on Jan. 23, 2002, now Pat. No. 6,770,093.

(51) Int. Cl.
*A61F 9/00* (2006.01)
(52) U.S. Cl. .................................... 606/107; 623/6.12
(58) Field of Classification Search ................. 606/107, 606/166, 170, 171; 604/22; 623/905, 906, 623/6.52, 6.12, 907, 6.36
See application file for complete search history.

(56) References Cited

U.S. PATENT DOCUMENTS

| 4,215,440 | A | | 8/1980 | Worst | |
|---|---|---|---|---|---|
| 5,098,439 | A | * | 3/1992 | Hill et al. | .................... 606/107 |
| 5,192,319 | A | | 3/1993 | Worst | |
| 5,226,908 | A | | 7/1993 | Yoon | |
| 5,669,923 | A | * | 9/1997 | Gordon | ...................... 606/170 |
| 5,676,669 | A | * | 10/1997 | Colvard | ...................... 606/107 |
| 6,152,959 | A | | 11/2000 | Portney | |
| 6,299,591 | B1 | * | 10/2001 | Banko | ......................... 604/22 |
| 6,338,710 | B1 | * | 1/2002 | Takahashi et al. | ............. 600/37 |
| 6,342,058 | B1 | | 1/2002 | Portney | |
| 6,558,400 | B2 | * | 5/2003 | Deem et al. | .................. 606/151 |
| 6,770,093 | B2 | * | 8/2004 | Worst et al. | ................ 623/6.12 |
| 6,837,848 | B2 | * | 1/2005 | Bonner et al. | ............... 600/114 |
| 2002/0116062 | A1 | | 8/2002 | Portney | |

OTHER PUBLICATIONS

Operaid Opthalmic Cannulae, Brochure of Opthec B.V., Groningen, The Netherlands, Jan. 1999.

* cited by examiner

*Primary Examiner*—Gary Jackson
*Assistant Examiner*—Victor X Nguyen
(74) *Attorney, Agent, or Firm*—Akerman Senterfitt

(57) ABSTRACT

For attaching an intraocular implant having pincher like clamping arms forming a pinching area between end portions of the clamping arms to an iris of an eye, the implant is positioned against a surface of the iris in the anterior chamber of the eye, a passage in a distal end portion of an ophthalmologic surgical instrument in the anterior chamber of the eye is positioned against a surface portion of the iris closely adjacent the pinching area, and suction is applied to the passage and at least one of the end portions of the clamping arms is urged towards the iris, causing a tuck of iris material adhered to the passage to be inserted into the pinching area. Thus, a tuck adhering to the passage can easily be introduced into the pinching area between the clamping arms. An instrument and an implant specifically adapted for this method are described as well.

10 Claims, 8 Drawing Sheets

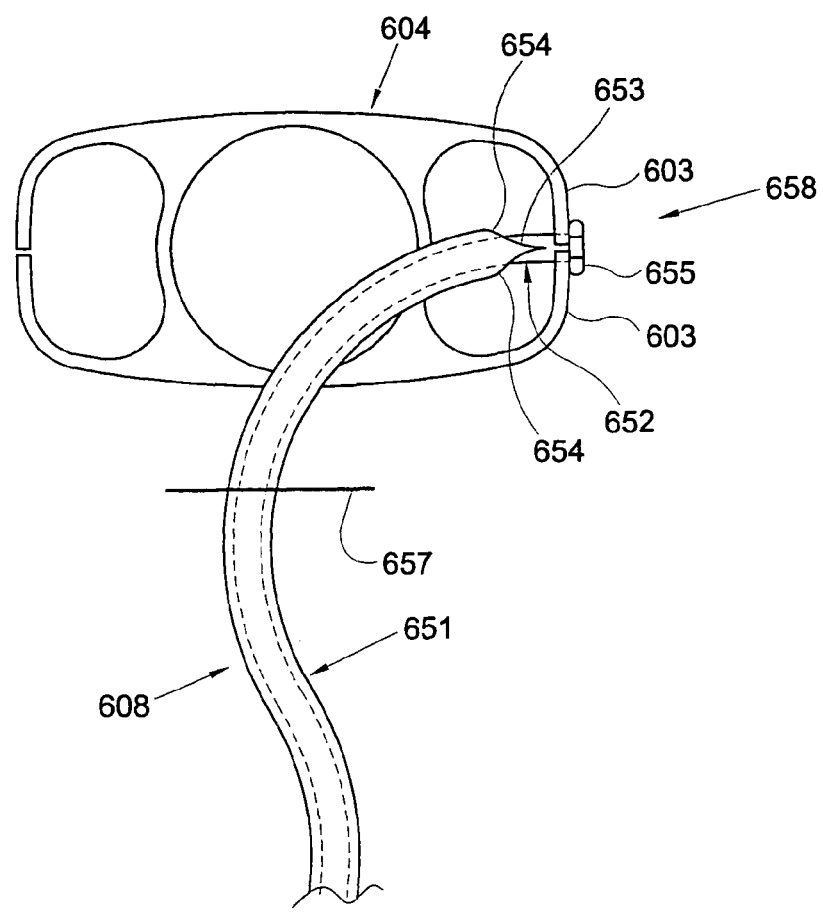
Fig. 18
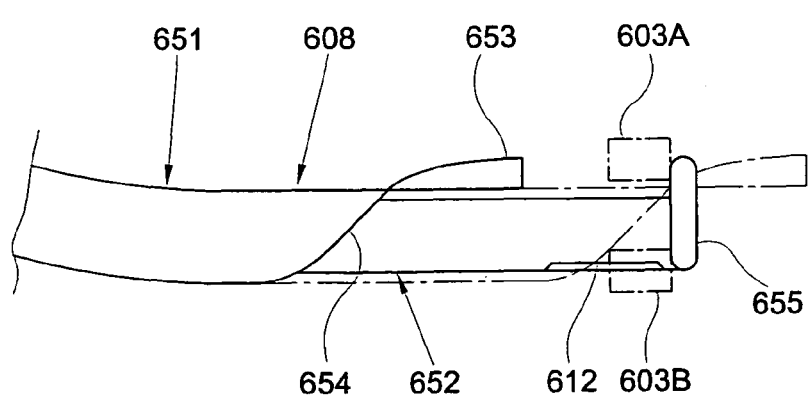 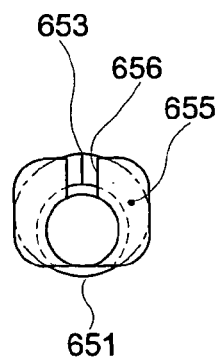
Fig. 19  Fig. 20

FIXATION OF AN INTRAOCULAR IMPLANT TO THE IRIS

CROSS REFERENCE TO RELATED APPLICATIONS

This application is a divisional of U.S. patent application Ser. No. 10/055,416 filed Jan. 23, 2002.

FIELD AND BACKGROUND OF THE INVENTION

The invention relates to a method and an instrument for inserting a tuck of iris tissue between clamping arms of an intraocular device to be attached to a surface of the iris in an anterior chamber of an eye. The invention also relates to an ophthalmologic implant to be attached by pinching a tuck of iris tissue.

In U.S. Pat. Nos. 4,215,440 and 5,192,319 intraocular lenses, are described which are to be implanted in the anterior chamber of the human eye by clamping a tuck of iris tissue between pincher-like arms projecting from an optical portion of the lens.

Advantages of attaching an intraocular lens to a plea of iris tissue are that the iris does not need to be perforated, that no parts of the lens project through the iris, that the attachment can be made quickly and with few manipulations, and that the attached lens is also secured against rotation about its optical axis. Forming a tuck of iris material is carried out by stroking iris tissue into a tuck and by bringing the tuck between ends of pincher-like arms projecting from the optical portion of the lens by, at the same time, pushing one of the clamping arms away from the iris relative to the other clamping arm so that the iris opens up. Although many eye surgeons routinely perform this technique, it requires special skill and training.

SUMMARY OF THE INVENTION

It is an object of the present invention to provide a solution which facilitates the formation of a tuck of iris tissue and the introduction of that tuck between the clamping arms of the implant.

According to the invention, this problem is solved by providing a method for attaching an intraocular implant having pincher-like clamping arms forming a pinching area between the clamping arms to an iris of an eye, including: positioning the implant against a surface of the iris in the anterior chamber; positioning a passage in a distal end portion of an ophthalmologic surgical instrument in the anterior chamber against the surface of the iris closely adjacent the pinching area; and applying suction to the passage and urging at least one of the end portions of the clamping arms towards the iris, causing a tuck of iris material adhered to the passage to be inserted into the pinching area.

The invention further provides an ophthalmologic surgical instrument for inserting a tuck of iris tissue in a pinching area between clamping arms of an intraocular implant to be attached to a surface of the iris in an anterior chamber of an eye, including: an elongate distal end portion for insertion into the anterior chamber, the distal end portion generally extending in an axial direction and comprising a laterally facing entry passage in a distal tip section of the distal end portion, the passage having an entry area bounded by a rim extending in a single plane for sealingly contacting the iris tissue surface and a crest facing away from and extending essentially parallel to the plane, for urging open the pinching area between the clamping arms, and a conduit extending from the passage for transferring a vacuum to the passage from at least a more proximal portion of the instrument. Such an instrument is specifically adapted for carrying out the method according to the invention.

Since the iris material is adhered to the passage of which the rim essentially sealingly contacts the iris tissue surface, a tuck adhering to the passage can easily be introduced into the pinching area between the clamping arms which are urged towards the iris by passing the crest of the distal end portion through pinching area between the clamping arms. The iris material follows the crest so that a tuck of the iris tissue is inserted between the clamping arms.

The invention further provides an intraocular implant having pincher-like clamping arms for engaging a tuck of iris tissue for attaching the implant to the surface of the iris in an anterior chamber of an eye, the pincher-like clamping arms projecting from a central portion of the implant, and defining a pinching area in a position spaced from the central portion, a gap being enclosed by the central portion and the clamping arms, the central portion having a positioning spot for positioning a tip of an ophthalmologic instrument in a position opposite across the gap of the pinching area between the clamping arms. Such an implant is specifically adapted for use in combination with an elaboration of the invention in which the clamping arms are urged towards the iris by the distal end portion of the instrument exerting a force towards the iris on a central portion of the implant while the crest thereof is passed through the pinching area between the clamping arms in a direction away from the implant. To facilitate keeping the tip of the distal end portion of the instrument exerting a force on the implant in a position relative to the implant, and thereby facilitate control over the position of the implant prior to its complete attachment to the iris, the implant is provided with a positioning spot for positioning the tip of the ophthalmologic instrument. This spot is engaged by the tip of the ophthalmologic instrument and makes it less prone to slipping over the surface of the implant.

Particular elaborations and embodiments of the invention are set forth in the dependent claims.

Further features, effects and details of the invention appear from the detailed description and the drawings. In the brief description, the orientation of views refers to an orientation of the eye and surgical instruments where the anterior side of the eye is facing vertically upwards.

BRIEF DESCRIPTION OF THE DRAWINGS

FIG. 18 is a top plan view of a distal end portion of a sixth example of an ophthalmologic instrument according to the invention operating on iris tissue and clamping arms of an implant, FIG. 19 is a side view of a tip section of the distal end portion shown in FIG. 18, and FIG. 20 is a frontal end view of the tip section according to FIG. 19.

DETAILED DESCRIPTION

Figure 1:
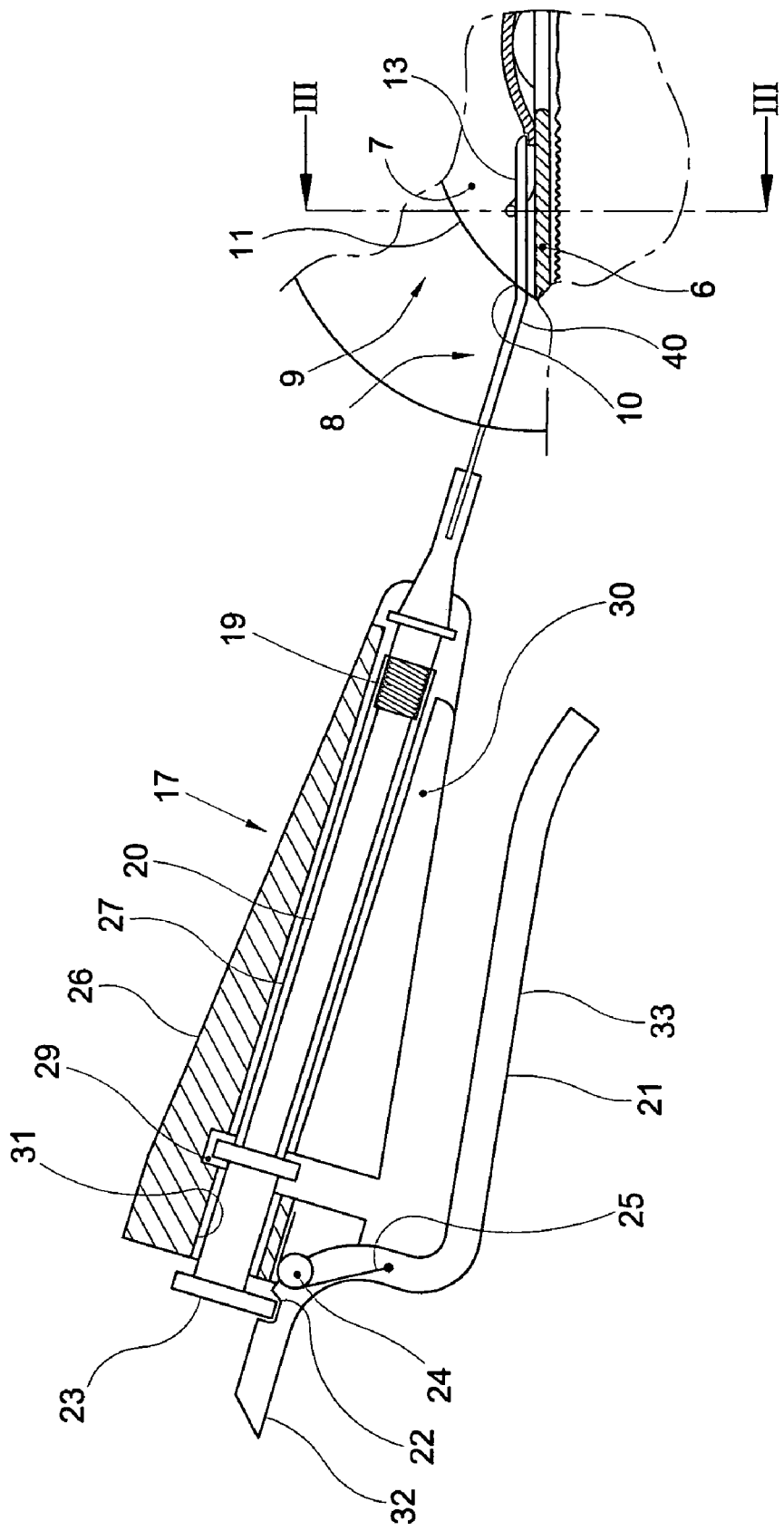
FIG. 1 is a partially enlarged and cut-off side view in cross-section of a first example of an ophthalmologic instrument according to the invention, with a distal end portion of the instrument inserted in the anterior chamber of an eye.

A first elaboration and embodiment of the invention is described with reference to FIGS. 1-3.

The main purpose of the present, proposed ophthalmologic surgical instrument is to insert a tuck of iris tissue 1 into a slit 2 between clamping arms 3 of an intraocular implant 4 to be attached to a surface 5 of the iris 6 in an anterior chamber 7 of an eye. Preferably, the clamping arms normally abut in the pinching area and the clamping force preferably varies relatively little with the distance between the pinching surfaces of the clamping arms 3. In FIG. 1—in which a distal end portion of the instrument is shown in an enlarged representation—the instrument is shown in operation in a situation in which the distal end portion 8 is inserted into the anterior chamber 7 of an eye 9 via an incision 10 in the cornea 11 of the eye. Preferably, such an incision is made in a portion of the cornea most closely and most remote from a vertical medial plane dividing the left and right half of the body.

The instrument has an elongate distal end portion 8 for insertion into the anterior chamber 7 of the eye. In the present example, the needle 8 generally extends in an axial direction and has a passage 12 in a distal tip section 13. The passage 12 has an entry facing laterally away from the central longitudinal axis of the needle in the area of the entry. The entry area is bounded by a rim 14 extending in a single plane 15 for essentially sealingly contacting the iris tissue surface 5 so that iris tissue adheres to the rim 14 of the passage 12 in response to suction applied to that passage 12. Furthermore, the needle has a clamping arm displacement crest 16 facing away from and extending essentially parallel to the plane 15. For inserting the tuck of iris material, the crest 16 urges the arms 3 apart to open the slit 2 to allow passage of the tip end section 13 into and through the slit 2 followed by a tuck of iris tissue 1 which is then released and left clamped in the slit 2.

For transferring a vacuum to the passage 12 from at least a more proximal portion of the instrument 17, a lumen 18 extends axially through the needle 8. The vacuum source communicating with the lumen 18 includes an energy storage in the form of a spring 19, a structure formed by a piston 20 for generating suction in response to releasing energy from the energy storage 19, and an operating structure in the form of a double lever 21 selectively pivotable from a position (as shown) retaining the piston 20 and a position in which the piston 20 is released, for releasing energy stored in the energy storage 19. Since the suction is generated in response to releasing stored potential energy, both operation and construction can be kept very simple. Because vacuum supply from an external source in not necessary, a connection to such a source can be dispensed with. This in turn contributes to the tidiness during surgery and facilitates the accurate control over the instrument.

The transfer of vacuum to the passage 12 can be damped, for instance by applying the vacuum via a restriction. Adherence of the iris tissue to the passage and formation of the tuck can thereby be carried out gradually, which facilitates control and improves adherences during the formation and insertion into the slit of the tuck of iris tissue.

The double lever is pivotally mounted to a housing 26 in which first a syringe 27 can be mounted via an open side 30. The operating flange 28 of the syringe is then received in a slit 29 in the housing. Next, the spring 19 and the piston 20 can be inserted into the syringe 27 via a passage 31 in the proximal end of the housing 26. For engaging the piston 20, the double lever has a recess 22 adapted for receiving an edge portion of an end plate 23 of the piston 20. The double lever is pivotable about an axis 24. A spring 25 urges the lever 21 into a position in which an arm 32 of the lever 21 at a proximal side of axis 24 is displaced towards the piston 20 for engaging the piston 20 and in which an operating arm 33 of the lever 21 extending along the housing 26 is in its position projecting from the housing 26. Pressing the operating arm 33 of the double lever 21 towards the housing 26 causes the double lever 21 to release the piston 20. This can be carried out with the hand that also holds the instrument.

Since the vacuum source includes an energy storage 19, a structure 20, 27 for generating suction in response to releasing energy from the energy storage 19 and an operating structure 21 for releasing energy stored in the energy storage 19, the instrument can be provided in the form of a compact self-contained unit which does not need to be connected to an external vacuum source.

This can moreover be realized in a simple construction since the suction generating structure has a suction chamber 27 having an internal volume bounded by a wall including a movable wall portion 20, and the energy storage is provided in the form of an elastic member 19 for urging the movable wall portion 20 into a direction causing the volume of the suction chamber to increase. Since the movable wall portion in the form of a piston 20 is axially movable in a channel, the conduit communicating with the channel across a closed end of the channel, allows the use of a conventional syringe, for instance a 1 ml syringe, as a disposable component of the proposed instrument.

The syringe also forms a control structure for displacing a limited volume (for instance at most less than 1 to 3 ml) of fluid during application of the vacuum. An advantage of limiting the amount of fluid displaced during application of suction to the passage 12 is, that the removal of undue amounts of liquid (which is usually gelled during intraocular surgery) out of the eye in the event the rim 14 does not seal adequately against the iris surface 5 is avoided, even if an initially strong vacuum is applied and the effective cross-sectional surface of the passage 12 is relatively large for effectively adhering iris tissue to the passage 12.

In use, attaching an implant 4 to the iris 6 using the instrument according to the present example is a carried out as follows: first the implant 4 is positioned against a surface 5 of the iris 6 in the anterior chamber 7 of the eye 9. Then, the passage 12 in the needle 8 is positioned in the anterior chamber 7 of the eye 9 against a surface portion 5 of the iris 6 closely adjacent the slit 2 between end portions of the clamping arms 3 to be attached to the iris 6. Then, suction is applied via the passage 12 and at least one of the end portions of the clamping arms 3 is urged towards the iris 6, causing a tuck of iris material 1 adhered to the passage 12 to be inserted into the slit 2. Finally, the instrument releases the tuck of iris material by removing the suction applied via the passage 12.

The crest 16 temporarily enlarges the slit 2 and succeeding portions of the needle 8 urging at least one of the clamping arms 3 away from the other clamping arm 3. This can for instance be carried out by pushing one end of one clamping arm 3 away from the other clamping arm 3 in an anterior direction with the crest 16 slightly off centre relative to the slit 2 so that it initially engages one clamping arm 3 only. Once the slit 2 is large enough, the tip end section of the needle 8 can be moved towards the other arm (i.e. to and slightly beyond the centre of the slit 2) entraining the tuck of iris material 1 into the slit 2.

The movement of the crest 16 in anterior direction relative to the clamping arms 3 can also be achieved by moving the crest 16 centrally into the slit 2 so that both clamping arms 3 are bent away from each other and the slit 2 is enlarged such that it accommodates to the needle 8 passing through.

It is observed that, preferably, the tuck of iris material 1 adhered to the passage 12 is not substantially displaced in anterior direction. The displacement of the arms 3 relative to the tuck of iris material 1 is preferably achieved by urging the arms 3 towards the iris 6 while the part of the needle 8 where the passage 12 adheres to the tuck of iris material 1 is retained in position. Thus, the arm or arms 3 of the implant are displaced in posterior direction while the needle 8 and the tuck of iris material 1 are held in an essentially stationary position in the eye 9.

To facilitate control over movements of the clamping arms 3 and the tuck of iris tissue 1 and to reduce the need of inserting several instruments into the eye 9 at the same time, the forces urging the end portion or end portions of the clamping arms 3 towards the iris 6 are preferably exerted on the implant 4 by the distal end portion 8 of the surgical instrument.

According to the present example, the forces for the urging the end portions of the clamping arms 3 towards the iris 6 are exerted on the implant 4 at a central portion 34 of the implant 4 in a position located on the side of the gap 36 opposite the side of the gap 36 where the slit 2 between the clamping arms 3 is located. This allows to urge the crest 16 into the slit 2 between the arms 3 and to urge the implant 4 towards the iris 6 with a single, slight tilting movement of the needle 8 during which the tip end moves in posterior direction relative to the section urging the clamping arms 3 apart. In the area of the incision 10, the needle 8 can in principle not move otherwise than axially, but the required tilting movement is very small and the iris 6 and the implant 4 can move slightly in posterior direction as the movement is made. Therefore, the required tilting movement of the needle 8 can be made without exerting undue stress on the cornea 11 in the area of the incision 10.

Figure 2:
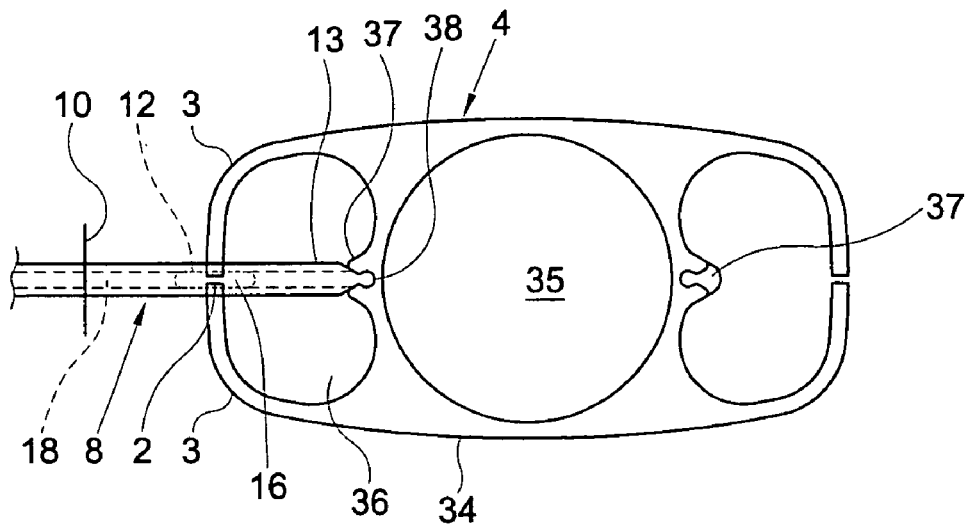
FIG. 2 is an enlarged top plan view of an intraocular implant according to the invention engaged by a distal end portion of an instrument according to the example shown in FIG. 1.
Figure 3:
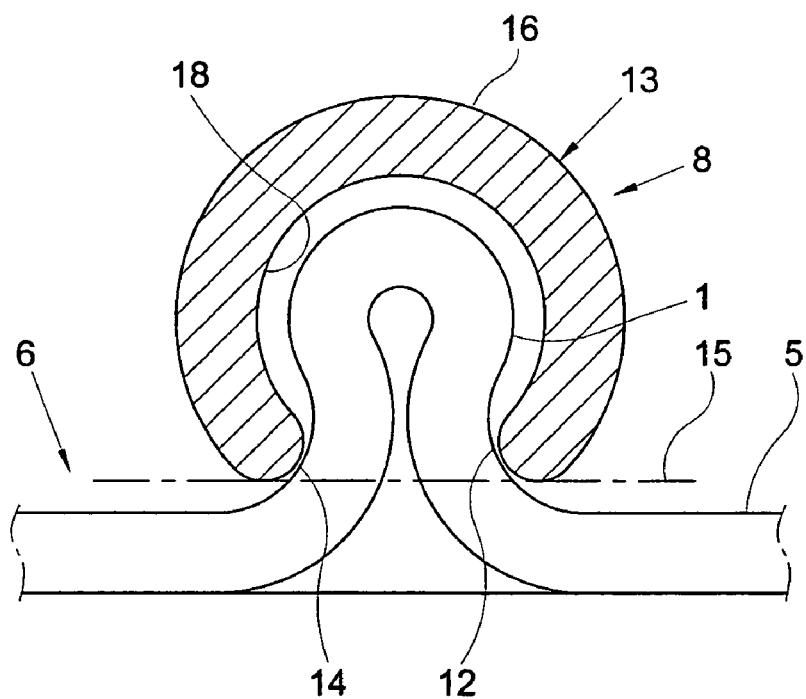
FIG. 3 is an enlarged cut-off view in cross-section along the line III-III in FIG. 1.

The implant shown in FIGS. 1-3 is specifically adapted for facilitating the technique according to this example of inserting a tuck of iris tissue 1 into the slit 2 between the clamping arms 3. To facilitate keeping the tip 38 of the needle 8 of the instrument exerting a force on the implant 4 in a position relative to the implant 4, and to thereby facilitate control over the position of the implant 4 prior to its complete attachment to the iris 6, the implant is provided with a positioning spot 37 for positioning the tip 38 of the ophthalmologic instrument. This spot 37 is engaged by the tip 38 of the ophthalmologic instrument and counteracts slipping of the tip 38 over the surface of the implant 4.

According to the present example, the positioning spot 37 is formed by a recess 37 adapted for receiving at least a portion of the tip 38 of the ophthalmologic instrument. Compared with a positioning spot formed by a projection, this is advantageous, because no complicated miniature structures need to be provided on the tip of the needle for receiving a projection. The recess 37 is open towards the slit 2. However, the recess can also be surrounded by a wall surrounding the entire recess so that a projection at the tip of the needle 8 can engage the recess to improve control over the position of the implant 4 prior to attachment to the iris 6 in every direction along the iris surface 5. The positioning spot can also be formed by a projection for engaging an eye in at least a portion of the tip of the ophthalmologic instrument.

To facilitate attaching the implant 4 to the iris 6 operating via an incision at the side of an eye facing the median longitudinal plane of the head, it is advantageous that the tip section 13 extends at an angle to a next, more proximal section 40. The tip section 13, which is intended to lie flat on the iris surface 5 with the rim 14 of the entry area that extends in a plane parallel to the tip section 13, preferably extends at an angle of up to 60.degree and preferably of 5-40.degree relative to the more proximal section 40 of the needle 8.

The length of the tip section 13 distal from the angled or curved portion of the needle is preferably at least 5 mm, so that the angled or curved portion and the more proximal section 40 extending at an angle to the tip section 13 remain outside the eye. This, in turn, is advantageous for preventing inadvertent contact of the needle 8 to the inside of the cornea.

Since the rim 14 around the entry extends in a plane 15 essentially parallel to the tip section 13 of the needle 8, it can easily be brought in sealing contact with the iris surface 5 by holding the needle 8 in such an orientation, that the tip section 13 extends along the surface 5 of the iris 6.

The tip end 37 of the needle 8 is closed and blunt, so that the risk of causing lesions on iris tissue 1 or the lens is reduced. By also providing that the tip is rounded, the risk of lesions is further reduced.

To increase the effective cross-sectional surface of the passage 12 while keeping the needle 8 slim, in particular in the section where the crest 16 to be passed through the slit 2 is located, the passage 12 has an elongate shape. An elongate shape of the passage 12 (length to width ratio preferably larger than 1:2 and more preferably at least 1:3 and preferably at most 1:8) is also advantageous, because the tuck to which the passage is to adhere is inherently elongate. The elongate shape of the passage also allows a crest portion of the tuck to be retained in the chamber behind the passage. The width of the passage 12 is preferably at least half the width of the needle in the area of the passage 12. To provide an effective sealing to the iris surface 5 while allowing iris tissue to slide smoothly into the passage 12, the rim 14 preferably has a rounded shape.

During the application of suction to the iris tissue 1, it is advantageous if it can easily be seen whether the iris tissue 1 actually adheres to the passage 12 and, where applicable, is drawn into the passage. To this end, at least the section of the needle 8 in the area of the passage 12 is transparent. This allows to visually monitor the effect of the applied suction and also provides feedback to the surgeon with respect to the need of moving the passage 12 further in posterior direction or of applying more suction. The transparent needle can for instance be made of high strength glass such as for instance Schott's DURAN, a borosilicate glass 3.3 (according to ISO 3585 and various national equivalents) or a suitable plastic material. It is also possible to improve visibility of the adherence of iris material by providing that not the whole needle or a tip section of the needle is transparent, but by providing a transparent window opposite the passage.

For allowing easy passage through the slit 2 between the clamping arms 3 of the implant and on the other hand providing a needle which is sufficiently stiff and which provides sufficient room for the passage and the lumen in the needle 8, the width of the section including the crest 16 is preferably less than 1 mm and more preferably between 0.2 and 0.5 mm. The needle thickness can for instance be in a range from 21-28 G and preferably 23-26 G. Moreover, the distal end portion in general will typically be free from cutting tools or any other tools.

Furthermore, according to the elaboration shown in FIGS. 1-3, the passage 12 against which the tuck of iris tissue 1 adheres is passed through the slit 2 (an alternative in which the passage does not pass through the slit is discussed below with reference to in FIGS. 10 and 11). An advantage of passing the area where the iris tissue 1 is held against the needle 8 through the slit 2 is that the introduction of iris material 1 into the slit 2 supports the formation of the tuck of tissue to be engaged by the clamping arms 3 exactly in the position of the slit 2.

Figure 4:
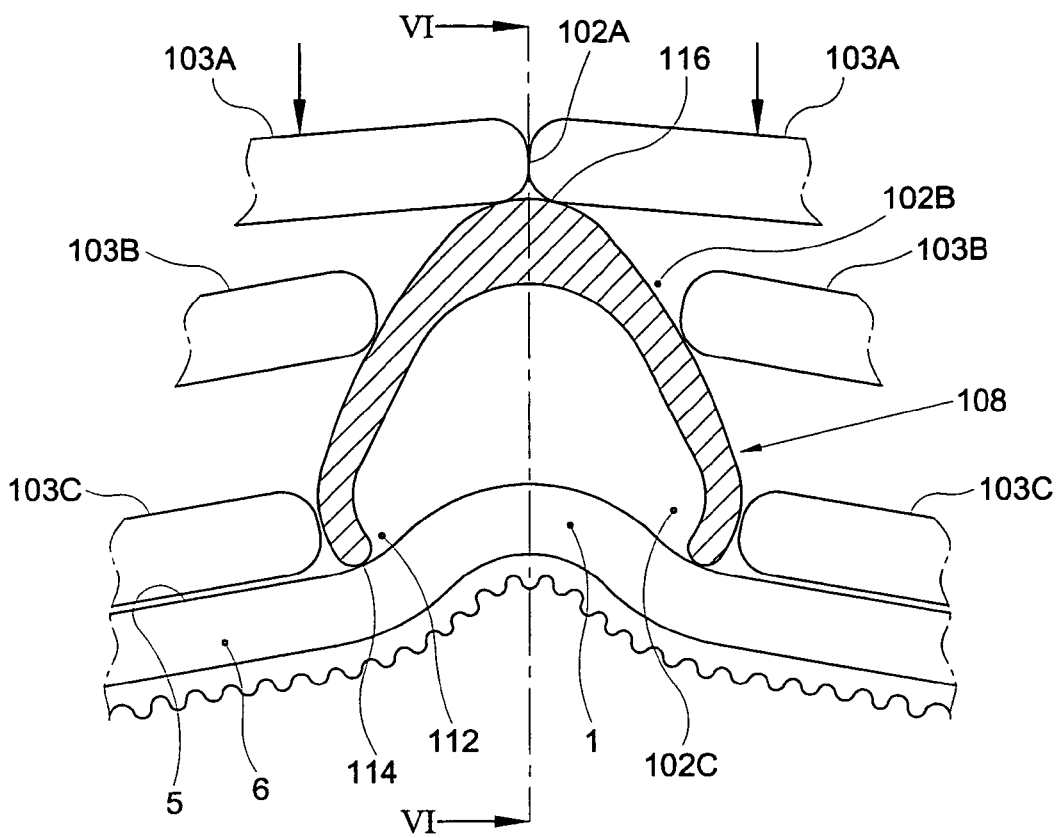
FIG. 4 is a view according to FIG. 3 showing a distal end portion of a second example of an ophthalmologic instrument according to the invention and shows end portions of clamping arms of an implant in successive stages.
Figure 5:
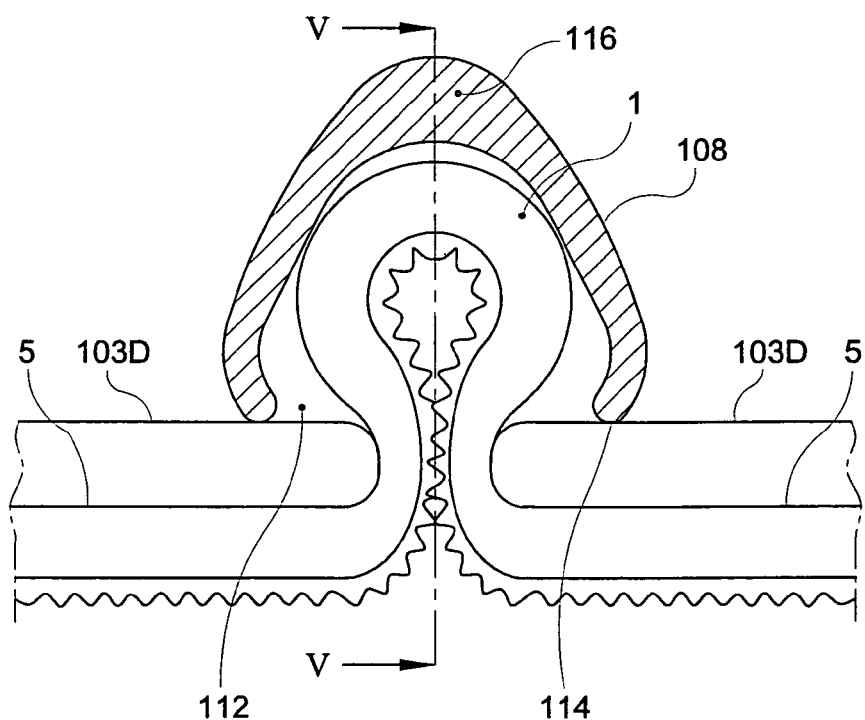
FIG. 5 is a view according to FIG. 4 in which the end portions of the clamping arms have reached an end stage clamping a plea of iris tissue.
Figure 6:
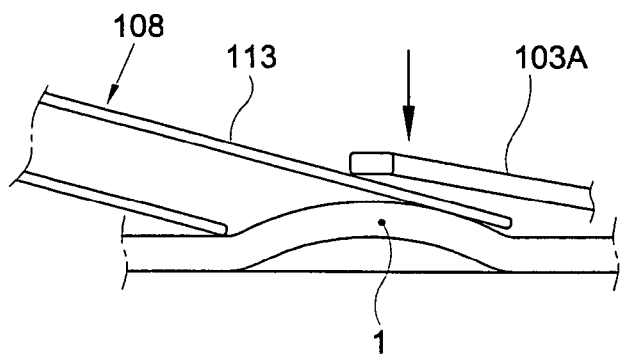
FIG. 6 is a side view in cross-section along the line VI-VI in FIG. 4

In FIGS. 4-6, one of the above-described examples of the process of passing the crest facing away from the passage through the slit while inserting a tuck of iris tissue into the slit is shown in more detail, the needle being of an instrument according to a second exemplary embodiment of the invention.

For passing the crest 116 of the needle 108 through the slit 102, the crest 116 is first positioned centrally behind the slit 102. Then, the clamping arms 103 are urged towards the iris 6 causing the tip ends of the arms 103 to be urged apart from positions 103A via positions 103B to a position 103C. In the positions 103C the tip ends of the clamping arms have been urged past the widest portion of the needle 8 and resiliently move towards each other again due to the elastic compression of the arms towards each other, until the situation shown in FIG. 5 is reached in which the clamping arms 103D clamp a tuck of the iris material 1. The clamping arms 103D in front of the passage 112 locally urge the iris surface 5 away from the rim 114 of the passage causing the adherence of iris material 1 to the passage 112 to break up.

Seen in cross-section perpendicular to the longitudinal direction of the tip section 113, the crest 116 has a substantially smaller radius of curvature than neighbouring portions of the needle 108. This feature facilitates entry of the crest 116 and subsequent portions of the needle into the slit, because of the essentially wedge-shaped cross-section of the portion of the needle 108, which is leading as the needle 108 is passed through the slit 102.

More specifically, at least in the section including the crest 116, the needle 8 has a generally triangular cross-section perpendicular to the longitudinal direction of that section of the needle 108. This provides the additional advantage, that essentially the maximum width of the needle is available for the passage 112 having a rim 114 in a flat plane to allow sealing contact with the iris surface 5 before the suction is applied. The wider the passage 112 is, the larger the iris surface portion is in which the suction applied via the passage 112 is operative and, accordingly, the more reliable the iris tissue can be made to adhere to the passage 112 in response to the applied suction.

Figure 7:
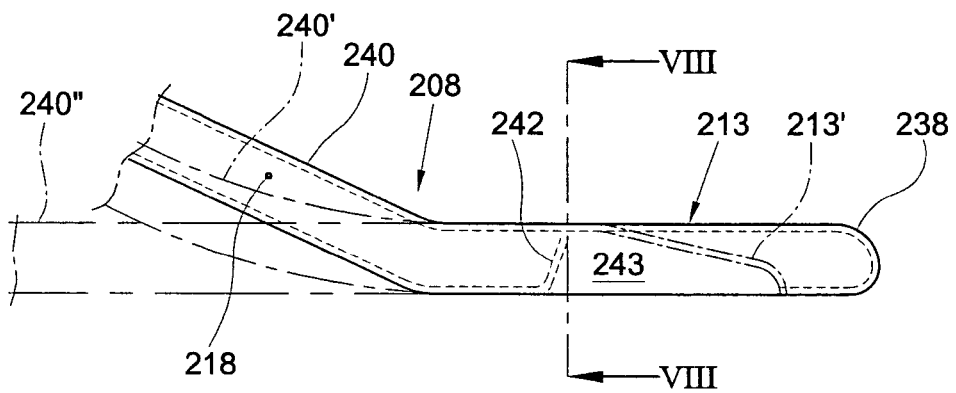
FIG. 7 is a cut-off side view of a distal end portion of a third example of an ophthalmologic instrument according to the invention.
Figure 8:
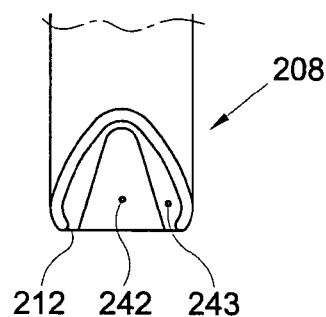
FIG. 8 is a view in cross-section along the line VIII-VIII in FIG. 7.
Figure 9:
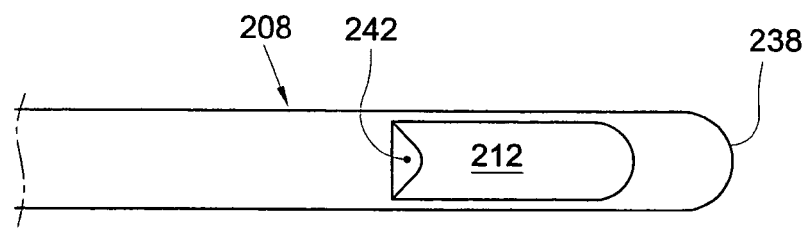
FIG. 9 is a bottom view of the distal end portion shown in FIGS. 7 and 8.

In FIGS. 7-9, a third example of a needle for an ophthalmologic surgical instrument according to the invention is described. As the needle shown in FIGS. 4 and 5, this needle 208 is based on a needle having a triangular cross-section. However, similar to the needle shown in FIGS. 1-3, the needle 208 according to this example has a tip section 213 that extends at an angle from a more proximal portion 240 of the needle 208. Some alternative possibilities for the path along which the more proximal portion of the needle extends are shown by dot and dash lines designated by reference numerals 240' and 240".

The passage 212 is manufactured by removing material from the bent distal end portion of the tip section 213. An alternative possibility of the shape of the tip section is shown by dot and dash lines designated by reference numeral 213".

In the lumen 218 closely adjacent the passage 212, a shield 242 is provided. This shield 242 bounds a tuck receiving chamber 243 behind the opening 212 for preventing iris tissue 1 from being aspired away from the passage 212 beyond the tuck receiving chamber 243, thereby reducing the risk of damage to the tissue. In this example, the shield 242 is provided in the form of a lip of wall material of the needle 208, which is bent into the lumen 218. However, it is also possible to provide the shield in others forms, such as in the form of a plug or grate which allows fluid to pass, but restrains iris tissue from being displaced beyond the shield.

Figure 10:
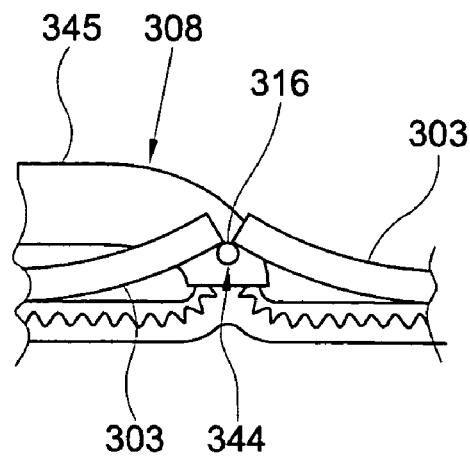
FIG. 10 is a side view in central cross-section across a distal end portion of a fourth example of an ophthalmologic instrument according to the invention operating on iris tissue and clamping arms of an implant.
Figure 11:
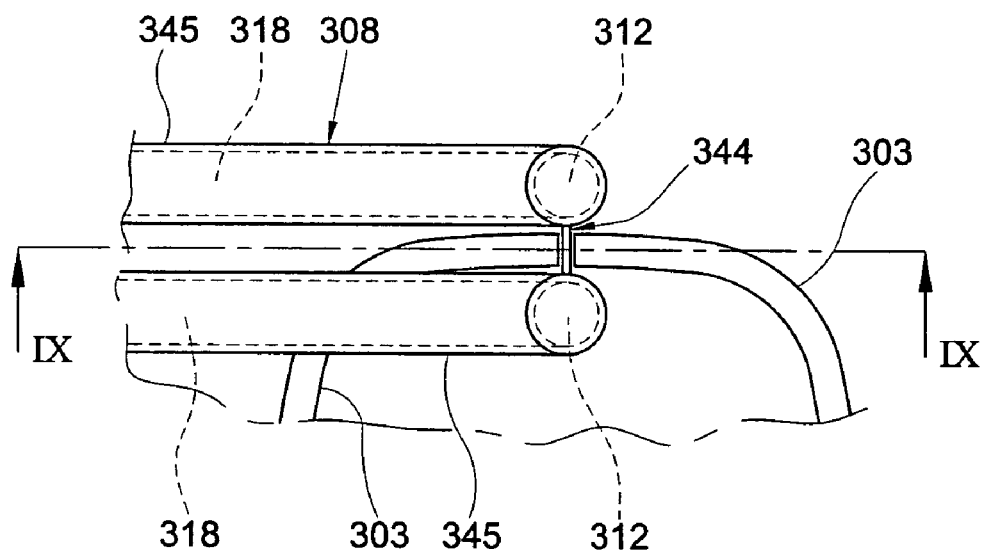
FIG. 11 is a top plan view of the situation according to FIG. 10.

In FIGS. 10 and 11 a fourth example of a needle for an instrument according to the invention is described in which the crest 316 is not located diametrically opposite of the passage. In this example, the needle 308 is of a twin barrel type and has two lumen 318 communicating with two passages 312. The crest 316 is part of a bar 344 interconnecting the two barrels 345 of the needle 308 and extends between the barrels 345. In operation, the tuck of iris material is formed and inserted as the iris tissue adheres to the passages 312 and the clamping arms 303 of the implant are moved towards the iris 6 and opened while the crest 316 and the bar 344 pass through the slit between the arms 303 (see FIG. 9).

Figure 12:
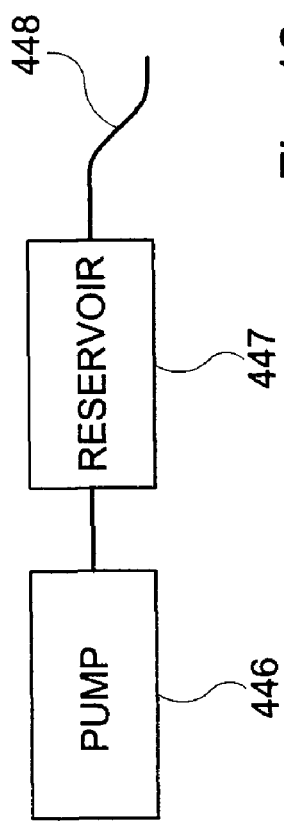
FIG. 12 is a schematic representation of a fifth example of an ophthalmologic instrument according to the invention.

FIG. 12 illustrates an example of an instrument according to the invention, which is adapted for injecting a liquid in the area where the tuck is to be formed prior to formation generating suction via the passages. According to this example, the needle 408 is connected to the vacuum source, which in this example is formed by a pump 446. In the conduit 418 between the pump 446 and the needle, a liquid reservoir 447 in incorporated. The pumping action of the pump 446 is reversible and can be adapted to inject a predetermined volume of liquid from the reservoir 447. The liquid reservoir can also form a chamber of the vacuum source, for instance as in the syringe shown in FIGS. 1-3 so that the need of a separate component is avoided. Provision of a separate, pre-filled reservoir cartridge can however, be advantageous to facilitate handling while ensuring sterile conditions. The liquid is preferably conventional saline and serves for displacing visco-elastic liquid such as HPMC (HydroxyPropylMethylCellulose) or Sodiumhyaluron in the area of the tuck to be formed to improve adherence of the iris tissue to the passage via which suction is applied and to reduce leakage between the rim of the passage and the surface of iris tissue.

The saline or another liquid introduced into the eye can also be advantageous for preventing under pressure which causes the cornea to buckle which in turn distorts the surgeon's vision into the anterior chamber of the eye. Liquid can be injected gradually during the application of suction, as a compensation for liquid withdrawn from the eye in the course of applying suction for adhering the needle to the iris surface. Alternatively, or in addition, a buffer dose of liquid can be injected into the eye for causing a temporary excess pressure and allowing the removal of some of the visco-elastic liquid before significant buckling of the cornea occurs.

Since the liquid reservoir 447 communicates with the passage in the needle 408 via which suction is applied to the iris tissue, a separate lumen or a separate insertion of an instrument for transporting the liquid to the eye is not necessary. However, it is also possible to provide a lumen for feeding liquid to the eye separate from the lumen communicating with the passage for providing a vacuum at the passage.

Figure 13:
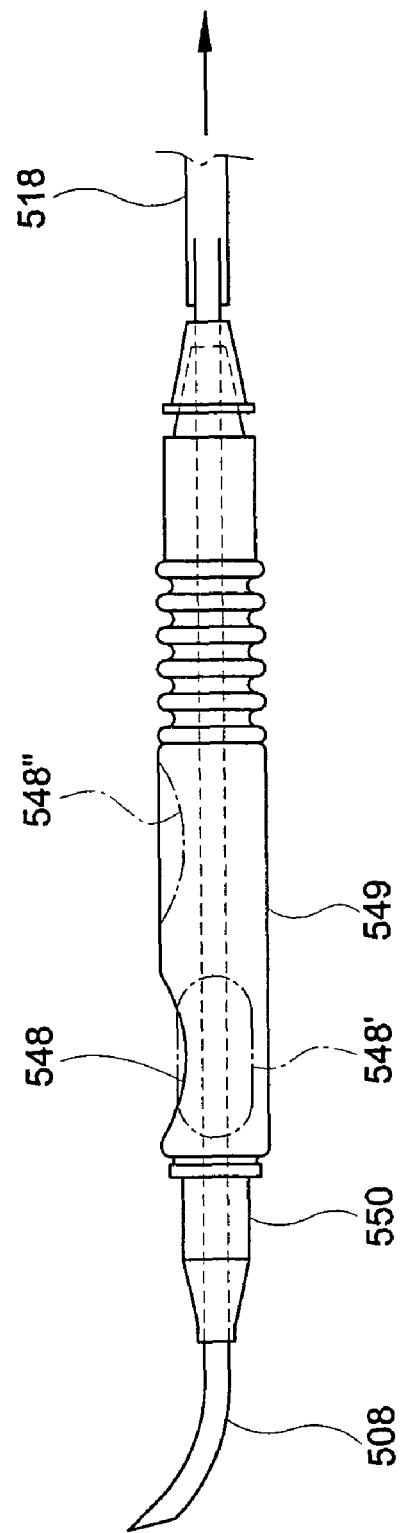
FIG. 13 is a side view of a sixth example of an ophthalmologic instrument according to the invention.

In FIG. 13 an example of an instrument according to the invention is shown in which the means for applying suction at the passage adjacent the tip of the needle 508 are formed by a conduit 518 which can be connected to a vacuum source. In use, the conduit 518 is preferably connected to a vacuum source, which is adjustable for varying the flow rate, the vacuum or both. For instance phako-emulsification apparatus typically includes a vacuum pump capable of providing a continuous (partial) vacuum. Thus, use can be made of a vacuum, which is typically present in an ophthalmologic surgery.

For controlling suction at the passage, a venting passage 548 communicating with the conduit 518 is provided, which can be closed selectively with the tip of a finger. The elongate grip 549 in which the venting passage 548 is provided is rotatable about it longitudinal axis relative to the needle 508 to allow the venting passage 548 to be located and oriented relative to the needle 508 in accordance with the surgeon's preferences and ergonomics, for instance to a position 548' indicated by dash and dot lines. To this end, the instrument includes a needle holder 550, which is rotatable relative to the grip 549 with such friction that the selected orientation of the needle 508 relative to the grip 549 is retained in use. The venting passage can also be provided in a more proximal position 548" also indicated by dash and dot lines, to be operated with the ring finger or the little finger.

A venting opening can also be applied advantageously in a device in which the vacuum is not permanent, such as the instrument shown in FIG. 13. In such instruments, the vent communicating with the conduit can for instance first be held in closed-off condition, the closure being released after insertion of the tuck of iris tissue.

Figure 14:
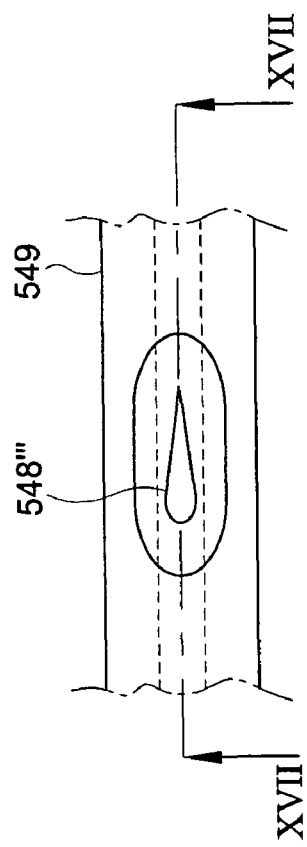
FIG. 14 is an enlarged top plan view of a portion of the instrument according to FIG. 13.
Figure 15:
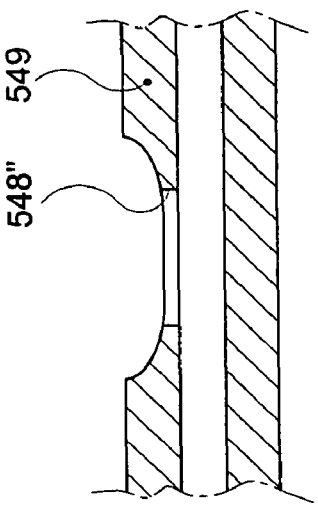
FIG. 15 is a side view along the line XV-XV in FIG. 14.

In FIGS. 14 and 15, a portion of the grip 549 in the area of the venting passage 548 is shown in more detail. In an area around the venting passage 548, the grip is flattened by forming a shallow trough 559 transversal to the axis of the grip. This allows the precise position of the surgeon's finger to be less critical for adequately closing off the passage 548.

Figure 16:
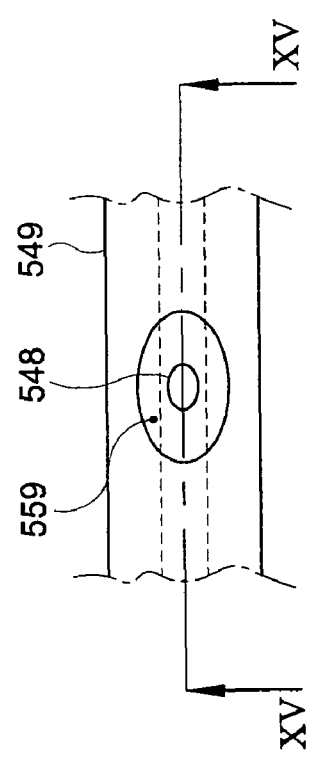
FIG. 16 is an enlarged top plan view of a portion of a variant of an instrument according to FIG. 13.
Figure 17:
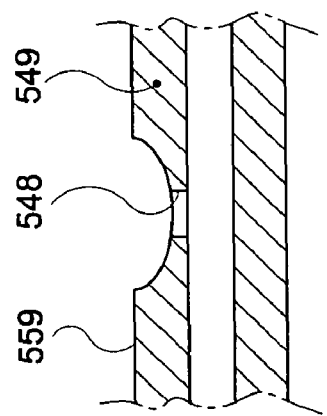
FIG. 17 is a side view along the line XVII-XVII in FIG. 14.

In FIGS. 16 and 17, the venting passage 548''' is elongate which facilitates dosage of the venting and thereby of the applied vacuum. To facilitate dosage when a very small venting flow is desired, the passage 548''' has a wide end and a narrow end. When venting via the narrow end, a given displacement of the finger partially closing off the venting passage in longitudinal direction of the passage's cross-section results in smaller variation in the venting flow than when venting via the wide end.

FIGS. 18-20 show a fifth example of a needle 608 for use in an instrument according to the invention. Also this needle 608 is adapted for exerting forces on the implant for urging at least one of the end portions of the clamping arms 603 towards the iris. According to this example, the needle 608 includes a sheath 651, which is axially and reciprocally movable over a core 652 of the needle 608 between a retracted position (shown in full lines) and a forward position (shown in dash and dot lines). The tip of the sheath includes a wedge 653 having a front edge extending radially relative to the core 652. From the front edge of the wedge, guide surfaces 654 forming the front end of the sheath 651 extend along opposite sides of the core 652 in proximal direction and about half the circumference of the core 652 and meet at the side of the core 652 facing away from the wedge 653. At the tip end of the core 652 a retainer 655 is arranged, which retainer includes a slot 656 dimensioned to receive a tip end of the wedge 653.

In use, the core 652 is positioned between the iris surface and the tip ends of the arms 603A of the implant 604 while the sheath 651 is in its retracted position. Next, the sheath 651 is urged to its forward position causing the guide surfaces to engage the tips of the arms 603. The retainer 655 prevents the tips of the arras from moving axially in distal direction in response to the forces exerted thereon by the guide surfaces 654. Thus, the guide surfaces 654 and the retainer 655 cooperate to urge the tips of the clamping arms 603 towards the position indicated with reference number 603B. In the meantime, iris tissue adheres to the passage 612 near the tip end of the needle and a tuck of the iris tissue is pinched between the ends of the arms 603 reaching a position between the core 652 of the needle 608 and the rest of the iris.

Since the distal end portion of the ophthalmologic surgical instrument exerts at least a portion of the forces towards the iris by engaging at least one of the end portions of the clamping arms 603, the forces are introduced near the position where the displacement is required, so that relatively small forces suffice for effecting the required displacement against elastic forces exerted by the material of the implant 604 and a very direct control of the displacements is obtained.

Moreover, the needle 608 of the ophthalmologic instrument according to this example is inserted via an incision 657 and is brought in a position extending from that incision 657 in a direction of a central portion of the implant 604 and curving away from the central portion towards at least one of the end portions of the clamping arms 603. This provides the advantage that both tucks at opposite ends of the implant 604 can be inserted operating via the same incision. A separate incision such as depicted at 658 in line with a longitudinal cross-section of the implant is therefore not required.

Although in the previous examples, the distal end portion is described as being formed by a needle, other generally elongate tubular forms of the distal end portion are conceivable as well, such as a flat strip or a flexible tube combined with an arm carrying the crest to be urged into the slit and the passage bounded by a rim to which the iris tissue to be inserted into the slit is to adhere. It is also noted that, in principle, each of the examples of the needles can be combined with each of the examples of the grips and means for applying and controlling the vacuum.

What is claimed is:

1. An ophthalmologic surgical instrument for inserting a tuck of iris tissue in a pinching area between clamping arms of an intraocular implant to be attached to a surface of the iris in an anterior chamber of an eye, comprising:
    an elongate distal end portion for insertion into the anterior chamber, said distal end portion comprising a laterally facing entry passage in an elongate distal tip section of the distal end portion, said distal tip section generally extending in an axial direction, said passage having an entry area bounded by a rim extending in a single plane for sealingly contacting the iris tissue surface, and an external crest facing away from and extending essentially parallel to said plane, for urging open the pinching area between the clamping arms; and a conduit extending from said passage for transferring a vacuum to said passage from at least a more proximal portion of the instrument;

wherein, in cross-sectional view of the distal tip section perpendicular to the axial direction, the crest has a substantially smaller radius of curvature than neighboring wall portions of the distal end portion.

2. An instrument according to claim 1, wherein in cross-sectional view of the distal tip section perpendicular to the axial direction, the distal tip section has a generally triangular outermost contour.

3. An ophthalmologic surgical instrument for inserting a tuck of iris tissue in a pinching area between clamping arms of an intraocular implant to be attached to a surface of the iris in an anterior chamber of an eye, comprising:

an elongate distal end portion for insertion into the anterior chamber, said distal end portion generally extending in an axial direction and comprising a laterally facing entry passage in a distal tip section of the distal end portion, said passage having an entry area bounded by a rim extending in a single plane for sealingly contacting the iris tissue surface and a crest facing away from and extending essentially parallel to said plane, for urging open the pinching area between the clamping arms; and a lumen extending from said passage for transferring a vacuum to said passage from at least a more proximal portion of the instrument; and a shield in said lumen closely adjacent said passage, said shield bounding a tuck receiving chamber behind the passage and extending transversely to said lumen proximally of said passage, for preventing iris tissue from being aspirated away from said passage beyond said tuck receiving chamber.

4. An ophthalmologic surgical instrument for inserting a tuck of iris tissue in a pinching area between clamping arms of an intraocular implant to be attached to a surface of the iris in an anterior chamber of an eye, comprising:

an elongate distal end portion for insertion into the anterior chamber, said distal end portion generally extending in an axial direction and comprising a laterally facing entry passage in a distal tip section of the distal end portion, said passage having an entry area bounded by a rim extending in a single plane for sealingly contacting the iris tissue surface, and an external crest facing away from and extending essentially parallel to said plane, for urging open the pinching area between the clamping arms; and a conduit extending from said passage for transferring a vacuum to said passage from at least a more proximal portion of the instrument, wherein said conduit and said distal end portion for insertion into the anterior chamber are free from cutting tools.

5. An instrument according to claim 4, wherein the distal tip section of the distal end portion extends at an angle to a next section of the distal end portion proximal of said tip section.

6. An instrument according to claim 4, wherein said rim extends in a plane essentially parallel to at least a tip section of said distal end portion.

7. An instrument according to claim 4, wherein said passage has an elongate shape.

8. An instrument according to claim 4, wherein said distal end portion is transparent in at least an area opposite said passage.

9. An instrument according to claim 4, wherein the tip end of the distal end portion is closed.

10. An instrument according to claim 4, wherein, at least in the section including said crest, said distal end portion has a width measured parallel to the rim of said passage, of less than 1 mm.

* * * * *